United States Patent [19]
Fujii et al.

[11] Patent Number: 4,507,301
[45] Date of Patent: * Mar. 26, 1985

[54] ANTI-CANCER COMPOSITION FOR DELIVERING 5-FLUOROURACIL

[75] Inventors: Setsuro Fujii, Toyonaka; Norio Unemi; Setsuo Takeda, both of Tokushima, all of Japan

[73] Assignee: Taiho Pharmaceutical Company, Limited, Tokyo, Japan

[ * ] Notice: The portion of the term of this patent subsequent to May 4, 1999 has been disclaimed.

[21] Appl. No.: 214,022

[22] Filed: Dec. 8, 1980

Related U.S. Application Data

[63] Continuation-in-part of Ser. No. 15,161, Feb. 26, 1979, which is a continuation-in-part of Ser. No. 891,343, Mar. 29, 1977, abandoned.

[30] Foreign Application Priority Data

Apr. 5, 1977 [JP] Japan ................................. 52-39341
Feb. 10, 1978 [JP] Japan ................................. 53-14676

[51] Int. Cl.$^3$ ........................................... A61K 31/505
[52] U.S. Cl. ..................................................... 514/274
[58] Field of Search ........................................ 424/251

[56] References Cited

PUBLICATIONS

Burcheual et al., Cancer Chemotherapy Repts., 6, pp. 1-5, (1960).
Chemical Abstracts, 81:99412t, (1974).
Sato et al., J. of Pharm. Sciences, 62, pp. 1975-1978, (Dec. 1973), 64, pp. 943-946, (Jun. 1975).

Primary Examiner—Jerome D. Goldberg
Attorney, Agent, or Firm—Murray and Whisenhunt

[57] ABSTRACT

An anti-cancer composition comprising a 5-fluorouracil (including derivatives thereof) and uracil (or salt thereof), is disclosed, wherein the composition contains less than 0.1 mole of the 5-fluorouracil per mole of the uracil.

9 Claims, No Drawings 4,507,301

ANTI-CANCER COMPOSITION FOR DELIVERING 5-FLUOROURACIL

CROSS-REFERENCE TO RELATED APPLICATIONS

This application is a continuation-in-part application of co-pending application Ser. No. 15,161 of Feb. 26, 1979, which was a continuation-in-part application of Ser. No. 891,343 of Mar. 29, 1977, now abandoned.

FIELD OF THE INVENTION

This invention relates to anti-cancer compositions and to methods of treating cancer, by delivering 5-fluorouracil to cancer tissue in a warm-blooded animal.

BACKGROUND OF THE INVENTION

Extensive research on the chemotherapy of cancers has heretofore been conducted, with the chemotherapy of cancers commenced in the latter half of the 1940's for the control of nucleic acid metabolism. As antimetabolites to nucleic acids, 6-mercaptopurine was synthesized first, followed by the discovery of 5-fluorouracil.

5-fluorouracil was synthesized by Duschinsky in 1957 and found to have anti-cancer activity by Heidelberger et al. The compound has a wide anti-cancer spectrum range, produces outstanding effects especially on adenocarcinomas and is therefore one of the anti-cancer agents which are most widely used for clinical purposes. Since 5-fluorouracil is typical of antagonists to nucleic acid metabolism, intensive research is still continued on compounds having 5-fluorouracil as the basic skeleton.

SUMMARY OF THE INVENTION

The present invention includes the method of treating cancer sensitive to 5-fluorouracil therapy in a warm-blooded animal by delivering 5-fluorouracil to such cancer in such animal by administering to the animal a therapeutically effective amount of the composition of the present invention. The present invention is thus an improvement over the invention described in our earlier U.S. patent application Ser. No. 15,161 of Feb. 26, 1979, the entire disclosure of which is hereby incorporated by reference for the teachings of the anti-cancer compositions and methods of treatment disclosed therein.

More specifically this invention provides anti-cancer compositions comprising uracil or a salt thereof, and at least one 5-fluorouracil selected from among compounds represented by the formula

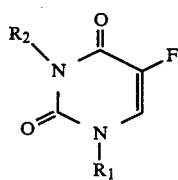

(I)

wherein $R_1$ and $R_2$ are the same or different and are each a hydrogen atom, tetrahydrofuryl, $C_2$–$C_{12}$ alkoxymethyl or $C_2$–$C_{12}$ alkylcarbamoyl, in a small amount of less than 0.1 mole per mole of the uracil or salt thereof.

DETAILED DESCRIPTION OF THE INVENTION

Salts of uracil which are useful for the present invention are those that are pharmacologically acceptable. Typical of such salts are alkali metal salts, especially the sodium salt and the potassium salt of uracil.

5-fluorouracils useful for the present invention are those represented by the formula (I). Alkoxymethyl groups represented by $R_1$ and $R_2$ of the formula (I) are preferably those having 2 to 6 carbon atoms, such as methoxymethyl, ethoxymethyl, butoxymethyl, etc. Preferred alkylcarbamoyl groups are those having 2 to 10 carbon atoms, such as methylcarbamoyl, isopropylcarbamoyl, butylcarbamoyl, hexylcarbamoyl, cyclohexylcarbamoyl, octylcarbamoyl, etc. Typical compounds represented by the formula (I) are:

5-fluorouracil (Compound 1)
1-(2-tetrahydrofuryl)-5-fluorouracil (Compound 2)
1,3-bis(2-tetrahydrofuryl)-5-fluorouracil (Compound 3)
1-n-hexycarbamoyl-5-fluorouracil (Compound 4)
1-ethoxymethyl-5-fluorouracil (Compound 5)
3-(2-tetrahydrofuryl)-5-fluorouracil (Compound 6)

Compounds 1 to 6 given above are prepared by known processes. For example, processes are disclosed in Published Examined Japanese Patent Application No. 3873/1961 for Compound 1, in Published Examined Japanese Patent Application No. 10510/1974 for Compound 2, in Published Unexamined Japanese Patent Application No. 50384/1975 for Compound 3, in Published Unexamined Japanese Patent Application No. 148365/1975 for Compound 4, in Published Unexamined Japanese Patent Application No. 37787/1975 for Compound 5, and in Published Unexamined Japanese Patent Application No. 68189/1977 for Compound 6.

For the preparation of the anti-cancer composition of this invention, the ratio of uracil or a salt thereof to a 5-fluorouracil varies with the kinds of the uracil salts and of the 5-fluorouracil compounds. Generally the latter should be used in a very small amount of less than 0.1 mole per mole of the former. Usually it is preferable to use at least 0.01 mole to less than 0.1 mole, more preferably up to 0.09 mole, of the latter per mole of the former.

When a 5-fluorouracil is admixed with uracil or a salt thereof in a very small amount of less than 0.1 mole per mole of the uracil or salt thereof according to the present invention, the uracil or salt thereof enables the 5-fluorouracil to produce a remarkably enhanced anti-cancer effect than when the 5-fluorouracil is used in larger amounts. Therefore, the 5-fluorouracil, which is the active component of the present composition, can be given at a reduced dose. Additionally the composition of this invention has the outstanding advantage that when tested in animals for toxicity in terms of variations in the body weight, the composition exhibits lower toxicity with a decrease in the dose of the 5-fluorouracil.

The anti-cancer compositions of this invention comprising a 5-fluorouracil and uracil or a salt thereof are useful for curing cancers in warm-blooded animals by delivering 5-fluorouracil to the cancer tissue. When the 5-fluorouracil component (i.e., a derivative of 5-fluorouracil) is converted to 5-fluorouracil per se in vivo, the presence of the uracil or salt thereof suppresses the decomposition and inactivation of the resulting 5-fluorouracil, consequently permitting the composition to produce an outstanding anti-cancer effect.

When at least one of $R_1$ and $R_2$ are tetrahydrofuryl, alkoxymethyl or alkylcarbamoyl (that is, for compounds other than 5-fluorouracil itself (Compound 1)), the 5-fluorouracil will function in the manner of a prodrug. That is, the 5-fluorouracil, such as Compounds 2, 3, 4, 5 or 6, in the composition of the present invention will be converted in the body to 5-fluorouracil. The concentration of 5-fluorouracil maintained in the cancer cellular tissue of test animals will be maintained for an extended period of time. When the 5-fluorouracil compound in the composition of the present invention is 5-fluorouracil (Compound 1) the presence of the uracil or salt thereof appears to suppress decomposition and inactivation of the 5-fluorouracil, so that a larger effective amount of the 5-fluorouracil is delivered to the cancer cellular tissue. The composition of the present invention thus functions as a delivery system for delivering 5-fluorouracil to a tumor in a patient. The tumors which respond to the present treatment are those tumors which are sensitive to 5-fluorouracil therapy. Thus cancers sensitive to 5-fluorouracil therapy are treated by administering to a patient having such cancer an effective amount of the composition of the present invention. As known to those in the art, the cancers which are sensitive to 5-fluorouracil therapy include breast cancer, cancer of the esophagus, lung cancer, liver cancer and cancers of the gastro-intestinal system, such as stomach cancer, cancers of the intestines, cancer of the rectum, and the like.

With the present invention, uracil or a salt thereof and a 5-fluorouracil can be mixed together in the form of a preparation for administration, or can be given individually. According to therapeutic purposes, the anti-cancer composition of this invention can be given in the form of various preparations, such as tablets, capsules, granules, etc., for oral administration, and injection solutions, suppositories, etc., for non-oral administration.

These preparations are formulated by usual methods using excipients or carriers heretofore used in the art. The amount of the 5-fluorouracil to be contained in the tablet, capsule, suppository or like administration unit, although variable with the kinds of the 5-fluorouracil and the other uracil component and not particularly limited, is usually about 1 to about 100 mg for oral administration, about 1 to about 250 mg for injection and about 5 to about 400 mg for suppositories. It is desirable that the present composition be given at a daily dose, calculated as the 5-fluorouracil, of about 1 to about 400 mg for oral administration, about 1 to about 1000 mg for injection and about 5 to about 1000 mg as suppositories, although the dose varies with the kinds of the uracil components.

Thus the present composition has a remarkable advantage in the delivery of 5-fluorouracil to cancer tissue in warm-blooded animals.

EXAMPLES OF THE INVENTION

Typical of anti-cancer compositions of the invention for delivering 5-fluorouracil to cancer tissue in warm-blooded animals are given below.

Preparation 1

| | |
|---|---|
| Compound 2 | 50 mg |
| Uracil | 340 mg |
| Lactose | 570 mg |
| Corn starch | 30 mg |
| Hydroxypropyl cellulose | 10 mg |
| Per wrapper | 1000 mg |

A granular preparation is formulated from the above ingredients in the proportions given.

Preparation 2

| | |
|---|---|
| Compound 3 | 50 mg |
| Uracil | 450 mg |
| Lactose | 62 mg |
| Magnesium stearate | 18 mg |
| Talc | 8 mg |
| Hydroxypropylmethyl cellulose | 12 mg |
| Per tablet | 600 mg |

Tablets are formulated from the above ingredients in the proportions given.

Preparation 3

| | |
|---|---|
| Compound 5 | 25 mg |
| Uracil | 350 mg |
| Lactose | 120 mg |
| Crystalline cellulose | 72 mg |
| Magnesium stearate | 33 mg |
| Per capsule | 600 mg |

An encapsulated preparation is formulated from the above ingredients in the proportions given.

Preparation 4

| | |
|---|---|
| Compound 6 | 20 mg |
| Uracil | 450 mg |
| Lactose | 172 mg |
| Magnesium stearate | 58 mg |
| Per capsule | 700 mg |

An encapsulated preparation is formulated from the above ingredients in the proportions given.

Preparation 5

| | |
|---|---|
| Compound 4 | 50 mg |
| Uracil | 330 mg |
| Lactose | 510 mg |
| Corn starch | 100 mg |
| Hydroxypropylmethyl cellulose | 10 mg |
| Per wrapper | 1000 mg |

A granular preparation is formulated from the above ingredients in the proportions given.

Preparation 6

| | |
|---|---|
| Compound 3 | 150 mg |
| Sodium salt of uracil | 900 mg |
| Witepsol W-35 | 950 mg |
| Per suppository | 2000 mg |

Suppositories are prepared from the above ingredients in the proportions given.

The anti-cancer effect of compositions of this invention for delivering 5-fluorouracil to cancer tissue in warm-blooded animals will be described below with reference to the following experimental example.

EXPERIMENTAL EXAMPLE

Compositions of this invention are tested for anti-cancer effect on sarcoma 180 and AH 130, using mice of ICR strain and rats of Donryu strain, respectively, with 6 animals in each group. Cancer cells in an amount of $10^6$ cells are subcutaneously transplanted in the back area of each animal. Twenty-four hours after the transplant, a composition prepared by dissolving or suspending a 5-fluorouracil and uracil in 5% aqueous solution of gum arabic in proportions listed below is orally given to each animal once daily for 7 consecutive days. On the 10th day after the transplant, each tumor is removed and weighed. The cancer inhibition ratio is calculated from the ratio of the average tumor weight of each test group to that of the control group. On the other hand, the average body weight of each test group is determined before the transplant and after the removal of tumor, in comparison with that of the control group, to indicate the toxicity of the composition in terms of the increase in the average body weight. The animals of the control group is treated in the same manner as above except that no composition is given. Tables 1 to 6 show the results.

TABLE 1

Anti-cancer effect of Compound 3 admixed with uracil

| Amount of Compound 3 per mole of uracil (mole) | Dose of Comp. 3 (mg/kg) | Effect on sarcoma 180 Inhibition ratio (%) | Gain in average body weight (g) | Effect on AH 130 Inhibition ratio (%) | Gain in average body weight (g) |
|---|---|---|---|---|---|
| Comparison | | | | | |
| Compound 3 only | 150 | 68 | 1.8 | 67 | 15 |
| | 100 | 60 | 1.8 | 53 | 33 |
| | 67 | 38 | 2.0 | 41 | 41 |
| | 44 | 24 | 4.9 | 30 | 43 |
| 0.1 | 32 | 66 | −3.4 | 78 | 2 |
| | 16 | 42 | 1.0 | 56 | 14 |
| | 8 | 28 | 3.3 | 19 | 26 |
| | 4 | 14 | 4.2 | 12 | 39 |
| Invention | | | | | |
| 0.08 | 16 | 67 | 2.8 | 67 | 24 |
| | 8 | 41 | 3.4 | 29 | 31 |
| 0.04 | 16 | 75 | 2.8 | 76 | 20 |
| | 8 | 53 | 3.6 | 58 | 36 |
| 0.02 | 16 | 81 | 3.1 | 76 | 24 |
| | 8 | 54 | 3.6 | 66 | 33 |
| | 4 | 38 | 4.6 | 33 | 40 |
| 0.015 | 16 | 84 | 2.8 | 83 | 23 |
| | 8 | 53 | 3.9 | 69 | 30 |
| 0.01 | 16 | 71 | 3.3 | 85 | 23 |
| | 8 | 63 | 4.6 | 71 | 43 |
| Control | 0 | — | 5.4 | — | 54 |

TABLE 2

Anti-cancer effect of Compound 6 admixed with uracil

| Amount of Compound 6 per mole of uracil (mole) | Dose of Comp. 6 (mg/kg) | Effect on sarcoma 180 Inhibition ratio (%) | Gain in average body weight (g) | Effect on AH 130 Inhibition ratio (%) | Gain in average body weight (g) |
|---|---|---|---|---|---|
| Comparison | | | | | |
| Compound 6 only | 64 | 79 | 0.4 | 89 | −11 |
| | 32 | 41 | 1.5 | 58 | 17 |
| | 16 | 33 | 3.2 | 29 | 28 |
| | 8 | 19 | 4.1 | 13 | 39 |
| 0.1 | 32 | 88 | −3.1 | 81 | −17 |
| | 16 | 84 | 0.6 | 42 | 11 |
| | 8 | 40 | 2.6 | 20 | 24 |
| Invention | | | | | |

TABLE 2-continued

Anti-cancer effect of Compound 6 admixed with uracil

| Amount of Compound 6 per mole of uracil (mole) | Dose of Comp. 6 (mg/kg) | Effect on sarcoma 180 Inhibition ratio (%) | Gain in average body weight (g) | Effect on AH 130 Inhibition ratio (%) | Gain in average body weight (g) |
|---|---|---|---|---|---|
| 0.08 | 16 | 97 | 1.8 | 57 | 23 |
| | 8 | 56 | 2.8 | 29 | 28 |
| 0.04 | 8 | 71 | 1.9 | 51 | 23 |
| | 4 | 59 | 3.8 | 29 | 32 |
| 0.02 | 8 | 75 | 2.4 | 49 | 24 |
| | 4 | 43 | 3.6 | 32 | 33 |
| 0.015 | 8 | 73 | 1.9 | 54 | 20 |
| | 4 | 39 | 3.8 | 24 | 38 |
| 0.01 | 8 | 74 | 2.3 | 51 | 32 |
| | 4 | 32 | 4.8 | 20 | 43 |
| Control | 0 | — | 5.0 | — | 43 |

TABLE 3

Anti-cancer effect of Compound 5 admixed with uracil

| Amount of Compound 5 per mole of uracil (mole) | Dose of Comp. 5 (mg/kg) | Effect on sarcoma 180 Inhibition ratio (%) | Gain in average body weight (g) | Effect on AH 130 Inhibition ratio (%) | Gain in average body weight (g) |
|---|---|---|---|---|---|
| Comparison | | | | | |
| Compound 5 only | 150 | 68 | 1.4 | 63 | 19 |
| | 100 | 47 | 3.2 | 49 | 28 |
| | 67 | 36 | 4.4 | 41 | 34 |
| | 44 | 15 | 4.5 | 14 | 49 |
| 0.1 | 32 | 74 | −4.8 | 72 | 5 |
| | 16 | 56 | 1.9 | 50 | 12 |
| | 8 | 19 | 2.9 | 17 | 24 |
| | 4 | 9 | 4.1 | 11 | 40 |
| Invention | | | | | |
| 0.08 | 16 | 62 | 2.4 | 65 | 14 |
| | 8 | 31 | 3.1 | 33 | 29 |
| 0.04 | 16 | 65 | 2.6 | 70 | 15 |
| | 8 | 41 | 4.1 | 41 | 27 |
| | 4 | 25 | 4.9 | 23 | 36 |
| 0.02 | 16 | 68 | 2.9 | 69 | 16 |
| | 8 | 50 | 4.1 | 48 | 24 |
| | 4 | 27 | 4.2 | 30 | 40 |
| 0.015 | 16 | 78 | 3.0 | 74 | 19 |
| | 8 | 33 | 2.9 | 44 | 38 |
| 0.01 | 16 | 59 | 3.2 | 69 | 26 |
| | 8 | 46 | 3.3 | 43 | 41 |
| Control | 0 | — | 4.3 | — | 43 |

TABLE 4

Anti-cancer effect of Compound 2 admixed with uracil

| Amount of Compound 2 per mole of uracil (mole) | Dose of Comp. 2 (mg/kg) | Effect on sarcoma 180 Inhibition ratio (%) | Gain in average body weight (g) | Effect on AH 130 Inhibition ratio (%) | Gain in average body weight (g) |
|---|---|---|---|---|---|
| Comparison | | | | | |
| Compound 2 only | 150 | 72 | 1.9 | 63 | 7 |
| | 100 | 51 | 3.7 | 50 | 17 |
| | 67 | 34 | 4.5 | 37 | 38 |
| | 44 | 13 | 5.0 | 20 | 46 |
| 0.1 | 32 | 70 | −4.1 | 76 | 6 |
| | 16 | 58 | 2.5 | 55 | 38 |
| | 8 | 16 | 3.7 | 15 | 41 |
| | 4 | 5 | 4.8 | 11 | 50 |
| Invention | | | | | |
| 0.08 | 16 | 64 | 3.1 | 66 | 39 |
| | 8 | 24 | 3.8 | 26 | 40 |
| 0.04 | 16 | 66 | 4.5 | 74 | 37 |
| | 8 | 47 | 4.4 | 54 | 41 |
| | 4 | 26 | 4.8 | 26 | 47 |
| 0.02 | 16 | 73 | 3.0 | 74 | 43 |
| | 8 | 51 | 4.5 | 64 | 41 |
| | 4 | 30 | 4.6 | 30 | 49 |

TABLE 4-continued

Anti-cancer effect of Compound 2 admixed with uracil

| Amount of Compound 2 per mole of uracil (mole) | Dose of Comp. 2 (mg/kg) | Effect on sarcoma 180 | | Effect on AH 130 | |
|---|---|---|---|---|---|
| | | Inhibition ratio (%) | Gain in average body weight (g) | Inhibition ratio (%) | Gain in average body weight (g) |
| 0.015 | 16 | 84 | 3.1 | 78 | 40 |
| | 8 | 32 | 3.9 | 64 | 48 |
| 0.01 | 16 | 62 | 3.0 | 76 | 39 |
| | 8 | 46 | 4.4 | 78 | 45 |
| Control | 0 | — | 4.6 | — | 51 |

TABLE 5

Anti-cancer effect of Compound 1 admixed with uracil

| Amount of Compound 1 per mole of uracil (mole) | Dose of Comp. 1 (mg/kg) | Effect on sarcoma 180 | | Effect on AH 130 | |
|---|---|---|---|---|---|
| | | Inhibition ratio (%) | Gain in average body weight (g) | Inhibition ratio (%) | Gain in average body weight (g) |
| Comparison | | | | | |
| Compound 1 only | 32 | 67 | −0.1 | 68 | −14 |
| | 16 | 32 | 2.3 | 47 | 16 |
| | 8 | 14 | 3.8 | 18 | 49 |
| | 4 | 8 | 4.3 | 7 | 53 |
| 0.1 | 8 | 42 | 1.5 | 40 | 19 |
| | 4 | 17 | 4.0 | 24 | 37 |
| | 2 | 6 | 4.5 | 17 | 48 |
| Invention | | | | | |
| 0.08 | 6 | 44 | 3.2 | 49 | 30 |
| | 4 | 23 | 4.1 | 30 | 53 |
| 0.04 | 6 | 51 | 2.8 | 59 | 28 |
| | 4 | 32 | 4.4 | 31 | 43 |
| 0.02 | 6 | 71 | 3.2 | 68 | 26 |
| | 4 | 54 | 4.4 | 40 | 44 |
| 0.015 | 6 | 64 | 3.3 | 64 | 30 |
| | 4 | 44 | 4.6 | 39 | 53 |
| 0.01 | 6 | 63 | 4.4 | 69 | 37 |
| Control | 0 | — | 5.0 | — | 68 |

TABLE 6

Anti-cancer effect of Compound 4 admixed with uracil

| Amount of Compound 4 per mole of uracil (mole) | Dose of Comp. 4 (mg/kg) | Effect on sarcoma 180 | | Effect on AH 130 | |
|---|---|---|---|---|---|
| | | Inhibition ratio (%) | Gain in average body weight (g) | Inhibition ratio (%) | Gain in average body weight (g) |
| Comparison | | | | | |
| Compound 4 only | 150 | 79 | 2.8 | 83 | 24 |
| | 100 | 63 | 3.6 | 69 | 36 |
| | 67 | 51 | 4.5 | 59 | 45 |
| | 44 | 42 | 4.0 | 41 | 44 |
| 0.1 | 32 | 73 | −2.1 | 80 | −5 |
| | 16 | 49 | 0.6 | 53 | 6 |
| | 8 | 38 | 2.7 | 39 | 24 |
| | 4 | 11 | 3.9 | 20 | 39 |
| Invention | | | | | |
| 0.08 | 16 | 69 | 1.3 | 61 | 19 |
| | 8 | 43 | 2.9 | 49 | 27 |
| | 4 | 30 | 4.0 | 33 | 37 |
| 0.04 | 16 | 80 | 1.7 | 72 | 23 |
| | 8 | 49 | 2.7 | 53 | 33 |
| 0.02 | 16 | 73 | 1.6 | 76 | 25 |
| | 8 | 51 | 3.9 | 56 | 42 |
| 0.015 | 16 | 64 | 1.9 | 63 | 27 |
| | 8 | 60 | 3.8 | 49 | 28 |
| 0.01 | 16 | 62 | 3.8 | 58 | 24 |
| | 8 | 53 | 3.7 | 40 | 43 |
| Control | 0 | — | 4.1 | — | 46 |

These tables reveal that the anti-cancer compositions of this invention produce exceedingly high effects than when the corresponding 5-fluorouracils are used singly or in larger amounts with uracil than in the present invention. For example, Compounds 2 to 5 as used in combination with uracil according to the present invention are comparable in anti-cancer effect (inhibition ratio) to the corresponding compounds as used singly when the former are given at about 1/10 the doses of the latter. With Compounds 1 and 6, the dose given according to the present invention is about 1/5 to about ⅓ the dose otherwise needed for producing an equivalent anti-cancer effect. The tables also indicate that a 5-fluorouracil incoporated in the composition of the invention is comparable in anti-cancer effect to the same compound as used with uracil in a higher amount of at least 0.1 per mole of uracil when the former is given at about ½, or less than ½, the dose in the latter case. Stated more specifically with reference to Table 1 for example, the composition containing Compound 3 in a higher proportion of 0.1 mole per mole or uracil achieves inhibition ratios of 66% for sarcoma 180 and 78% for AH 130 when given at a dose of 32 mg/kg calculated as Compound 3. In contrast, the composition containing Compound 3 in a low proportion of 0.01 to 0.08 mole per mole of uracil achieves corresponding inhibition ratios of 67 to 84% and 67 to 85% when given at a dose of 16 mg/kg, i.e., one half the former dose. Further while an inhibition ratio of 68% is achieved by the single use of Compound 3 at a dose of 150 mg/kg, an equivalent effect can be achieved by the present invention with a dose of 16 mg/kg which is about 1/10 of the former.

Determination of concentrations of 5-fluorouracil in the blood and cancer tissues Ascites cells ($5 \times 10^6$) of AH-130 are subcutaneously transplanted in the armpit portion of male rats of Donryu strain weighing about 200 g. Seven days thereafter, the rats with cancer cells weighing at least 2 g are used, five rats in each group.

An anti-cancer composition comprising a 5-fluorouracil (a) alone or in combination with uracil (b) in the proportion(s) listed in Table 7 is suspended in a 5% solution of gum arabic immediately before use, and the suspension is orally given to the animal at the listed dose. One, two, four and eight hours after the administration, the blood serum and cancer tissue homogenate are collected, each of which is acidified with hydrochloric acid and extracted with chloroform. The resulting aqueous layer is examined for antibiotic activity according to the thin-cup method (Media Circle, Vol. 92, p. 259, 1967) with use of *Staphylococcus aureus* 209P strain. The results are given in Table 7 in terms of 5-fluorouracil concentration.

TABLE 7

| 5-Fluorouracil (a) Compd. No. | dose (mg/kg) | 5-FU (a)/ uracil (mol ratio) | Concentration of 5-fluorouracil | | | | | | | |
|---|---|---|---|---|---|---|---|---|---|---|
| | | | In blood (µg/ml) | | | | In cancer tissues (µg/g) | | | |
| | | | 1 hr | 2 hr | 4 hr | 8 hr | 1 hr | 2 hr | 4 hr | 8 hr |
| 1 | 8 | 5-FU only | 0.215 | 0.061 | 0.009 | 0.003 | 0.244 | 0.136 | 0.068 | 0.033 |
| | | 0.09 | 0.340 | 0.077 | 0.011 | 0.004 | 0.306 | 0.149 | 0.077 | 0.040 |
| | | 0.02 | 0.428 | 0.109 | 0.015 | 0.005 | 0.344 | 0.177 | 0.088 | 0.046 |
| 2 | 8 | 5-FU only | 0.035 | 0.023 | 0.009 | 0.004 | 0.039 | 0.027 | 0.017 | 0.012 |
| | | 0.09 | 0.124 | 0.065 | 0.009 | 0.005 | 0.156 | 0.139 | 0.074 | 0.042 |
| | | 0.02 | 0.194 | 0.153 | 0.023 | 0.008 | 0.195 | 0.146 | 0.082 | 0.048 |
| 3 | 8 | 5-FU only | 0.095 | 0.041 | 0.013 | 0.007 | 0.079 | 0.081 | 0.039 | 0.024 |
| | | 0.09 | 0.265 | 0.068 | 0.027 | 0.008 | 0.220 | 0.135 | 0.050 | 0.027 |
| | | 0.02 | 0.343 | 0.129 | 0.050 | 0.008 | 0.250 | 0.214 | 0.086 | 0.040 |
| 4 | 8 | 5-FU only | 0.054 | 0.044 | 0.021 | 0.009 | 0.063 | 0.074 | 0.059 | 0.045 |
| | | 0.09 | 0.096 | 0.059 | 0.024 | 0.010 | 0.168 | 0.128 | 0.078 | 0.052 |
| | | 0.02 | 0.128 | 0.091 | 0.085 | 0.013 | 0.298 | 0.148 | 0.125 | 0.083 |
| 5 | 8 | 5-FU only | 0.034 | 0.026 | 0.010 | 0.005 | 0.036 | 0.028 | 0.010 | 0.008 |
| | | 0.09 | 0.083 | 0.041 | 0.043 | 0.006 | 0.156 | 0.132 | 0.077 | 0.039 |
| | | 0.02 | 0.130 | 0.081 | 0.078 | 0.008 | 0.186 | 0.176 | 0.094 | 0.043 |
| 6 | 8 | 5-FU only | 0.093 | 0.070 | 0.014 | 0.007 | 0.083 | 0.081 | 0.077 | 0.036 |
| | | 0.09 | 0.203 | 0.103 | 0.017 | 0.008 | 0.229 | 0.166 | 0.126 | 0.046 |
| | | 0.02 | 0.299 | 0.184 | 0.028 | 0.011 | 0.262 | 0.175 | 0.161 | 0.052 |

We claim:

1. An anti-cancer composition for delivering 5-fluorouracil to cancer tissues in a warm-blooded animal, wherein the cancer is a cancer sensitive to 5-fluorouracil, said composition comprising uracil or a pharmaceutically acceptable salt thereof and 1-(2-tetrahydrofuryl)-5-fluorouracil, in an amount of about 0.01 to less than 0.1 mole per mole of the uracil or salt thereof.

2. An anti-cancer composition as defined in claim 1 wherein the salt of uracil is an alkali metal salt.

3. An anti-cancer composition as defined in claim 2 wherein the alkali metal salt is sodium or potassium salt.

4. An anti-cancer composition as defined in claim 1 wherein 0.01 to 0.09 mole of the 5-fluorouracil is used per mole of the uracil or salt thereof.

5. An anti-cancer composition as defined in claim 1 which is an oral preparation.

6. An anti-cancer composition as defined in claim 1 which is an injection preparation.

7. An anti-cancer composition as defined in claim 1 which is a suppository.

8. A method of delivering 5-fluorouracil to a cancer sensitive to 5-fluorouracil in a warm-blooded animal, said method comprising administering to the animal the anti-cancer composition of any one of claims 2-7 or 1 in the form of a single preparation in an amount which is effective to deliver an anti-cancer effective amount of 5-fluorouracil to the cancer.

9. A method of delivering 5-fluorouracil to a cancer sensitive to 5-fluorouracil in a warm-blooded animal, the method comprising administering to said animal in separate doses uracil or a pharmaceutically acceptable salt thereof and 1-(2-tetrahydrofuryl)-5-fluorouracil wherein about 0.01 to less than 0.1 mole of 1-(2-tetrahydrofuryl)-5-fluorouracil is used per mole of the uracil or salt thereof, in an amount which is effective to deliver an anti-cancer amount of 5-fluorouracil to the cancer.

* * * * *